(12) United States Patent
Sutter

(10) Patent No.: US 6,386,877 B1
(45) Date of Patent: May 14, 2002

(54) IMPLANT FOR HOLDING AND/OR FORMING A DENTAL PROSTHESIS OR ARTIFICIAL FINGER JOINT

(76) Inventor: Franz Sutter, Bennwilerstrasse 42, CH-4435, Niederdorf (CH)

(*) Notice: Subject to any disclaimer, the term of this patent is extended or adjusted under 35 U.S.C. 154(b) by 0 days.

(21) Appl. No.: 09/744,689

(22) PCT Filed: Jul. 29, 1999

(86) PCT No.: PCT/CH99/00357

§ 371 Date: Jan. 29, 2001

§ 102(e) Date: Jan. 29, 2001

(87) PCT Pub. No.: WO00/06043

PCT Pub. Date: Feb. 10, 2000

(30) Foreign Application Priority Data

Jul. 30, 1998 (CH) .............................................. 1596/98

(51) Int. Cl.[7] .............................. A61C 8/00; A61F 2/42
(52) U.S. Cl. .................................... 433/173; 623/21.15
(58) Field of Search ................................ 433/173, 174, 433/175, 176, 201.1; 623/21.15, 21.16, 21.17

(56) References Cited

U.S. PATENT DOCUMENTS 4,447,209 A     5/1984  Sutter ......................... 433/173
4,773,858 A  *  9/1988  Marquez ...................... 433/173
4,915,628 A  *  4/1990  Linkow et al. ............. 433/173
5,342,199 A  *  8/1994  Gillespie ..................... 433/173
5,370,695 A  * 12/1994  Meuli et al. ................... 623/16
5,417,692 A  *  5/1995  Goble et al. ................... 606/73
5,427,526 A  *  6/1995  Fernandes .................... 433/173

FOREIGN PATENT DOCUMENTS

DE    43 42 468 A1     6/1994
EP       00 169 976     2/1986
FR        2 084 522    12/1971
GB      2 210 795 A     6/1989

* cited by examiner

Primary Examiner—John J. Wilson
(74) Attorney, Agent, or Firm—Venable; Norman N. Kunitz; Catherine M. Voorhees

(57) ABSTRACT

The implant (11) has an anchoring part (15) with an axis (13), a generally cylindrical section and a peripheral surface (21). The latter is provided, in the generally cylindrical section, with protuberances (27) which are distributed around the axis (13). At least the majority of these protuberances are elongate and parallel with the axis (13) and have at least one terminal surface which is contiguous with a recess (23) having a base formed by the peripheral surface (21). In this way, the anchoring part (15) can be pushed into a substantially cylindrical hole (2) in a bone (1) such that the implant (11) is immediately anchored in the bone (1) in a stable manner, said implant nevertheless having a high degree of strength.

20 Claims, 8 Drawing Sheets

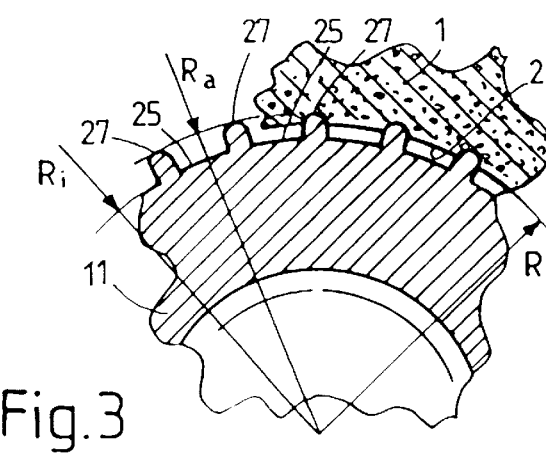
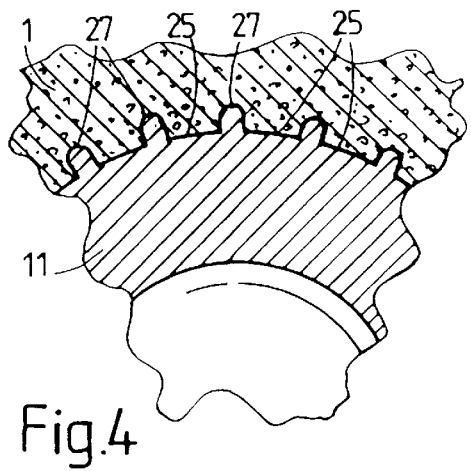
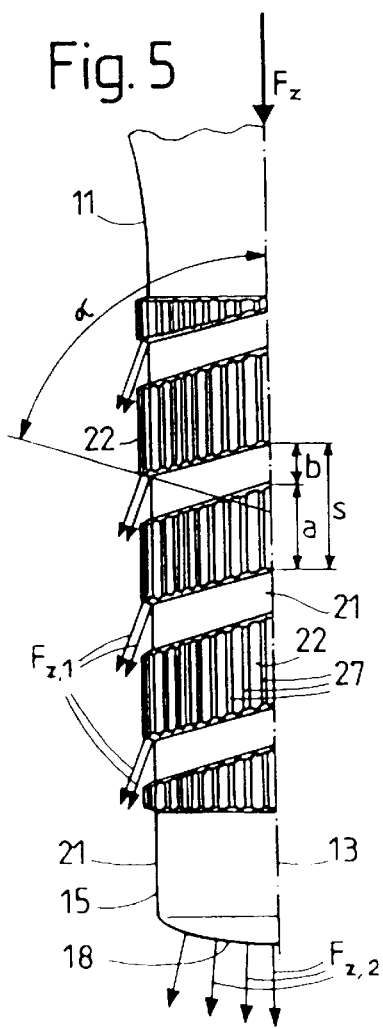
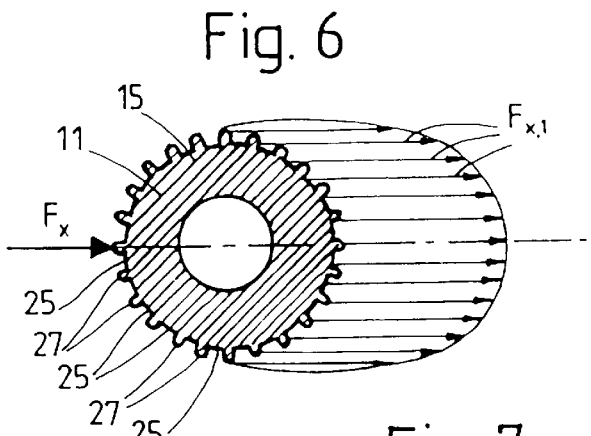
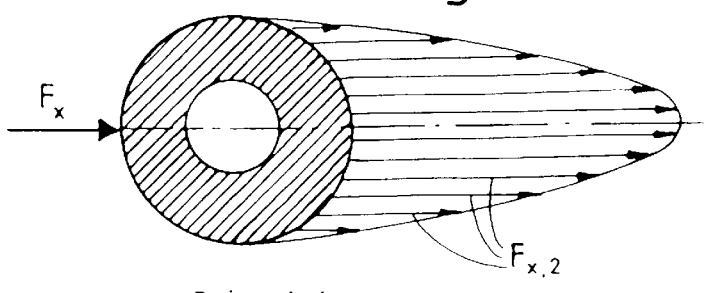
Fig. 3
Fig. 4
Fig. 5
Fig. 6
Fig. 7
Prior Art

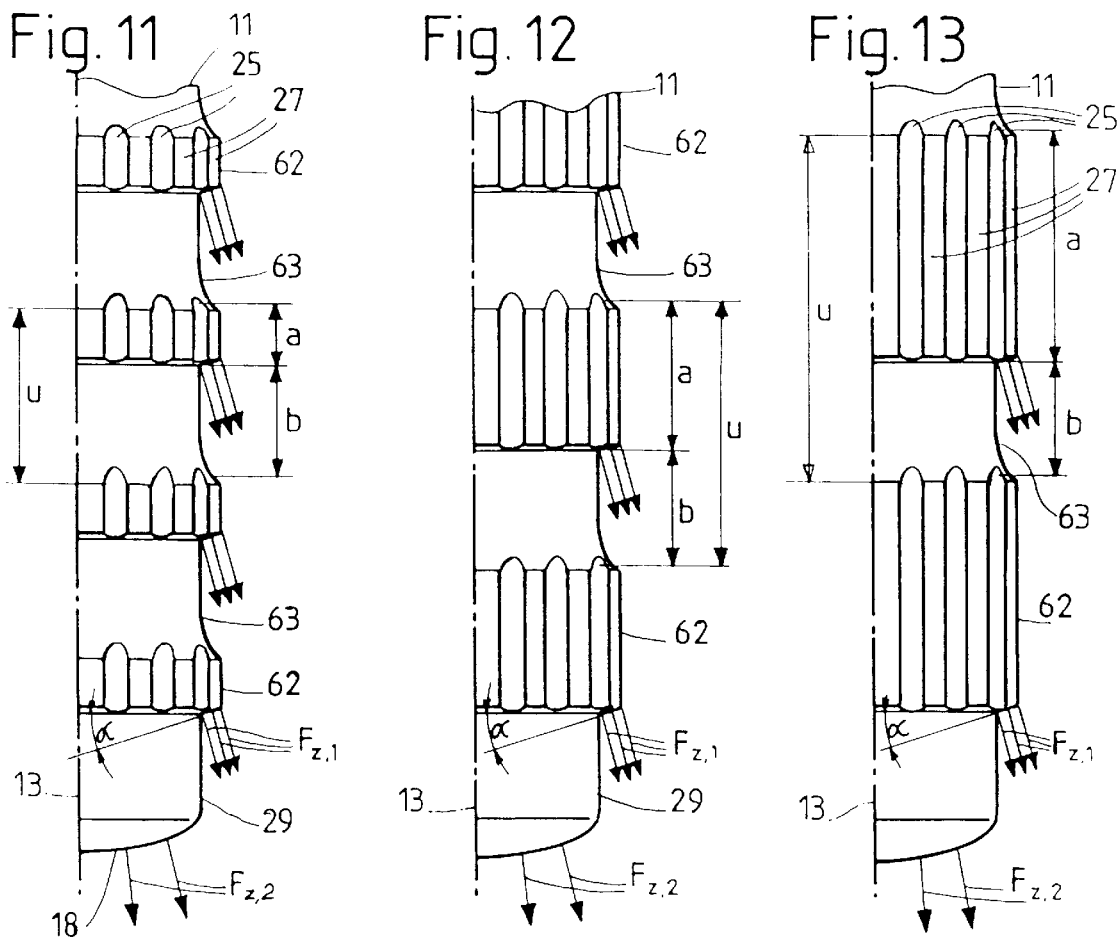
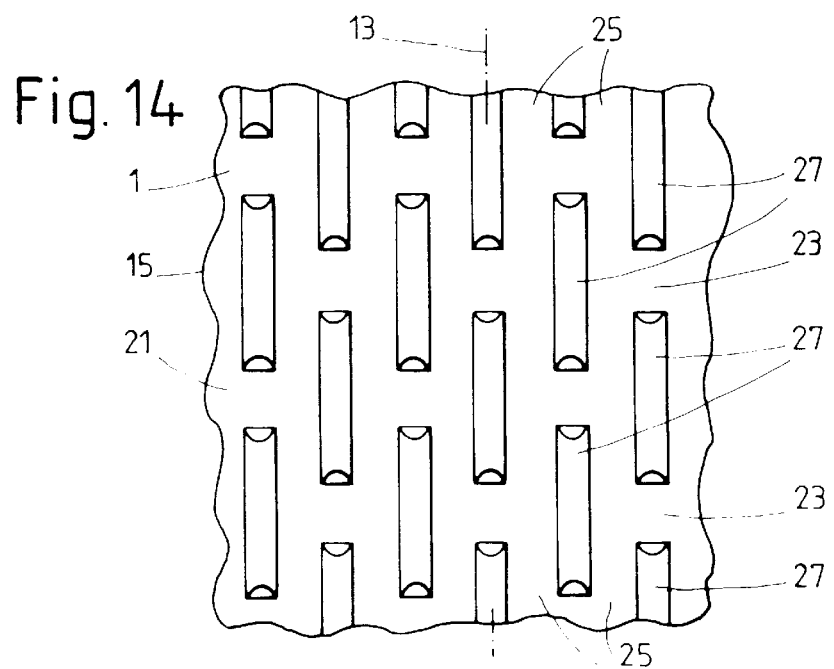

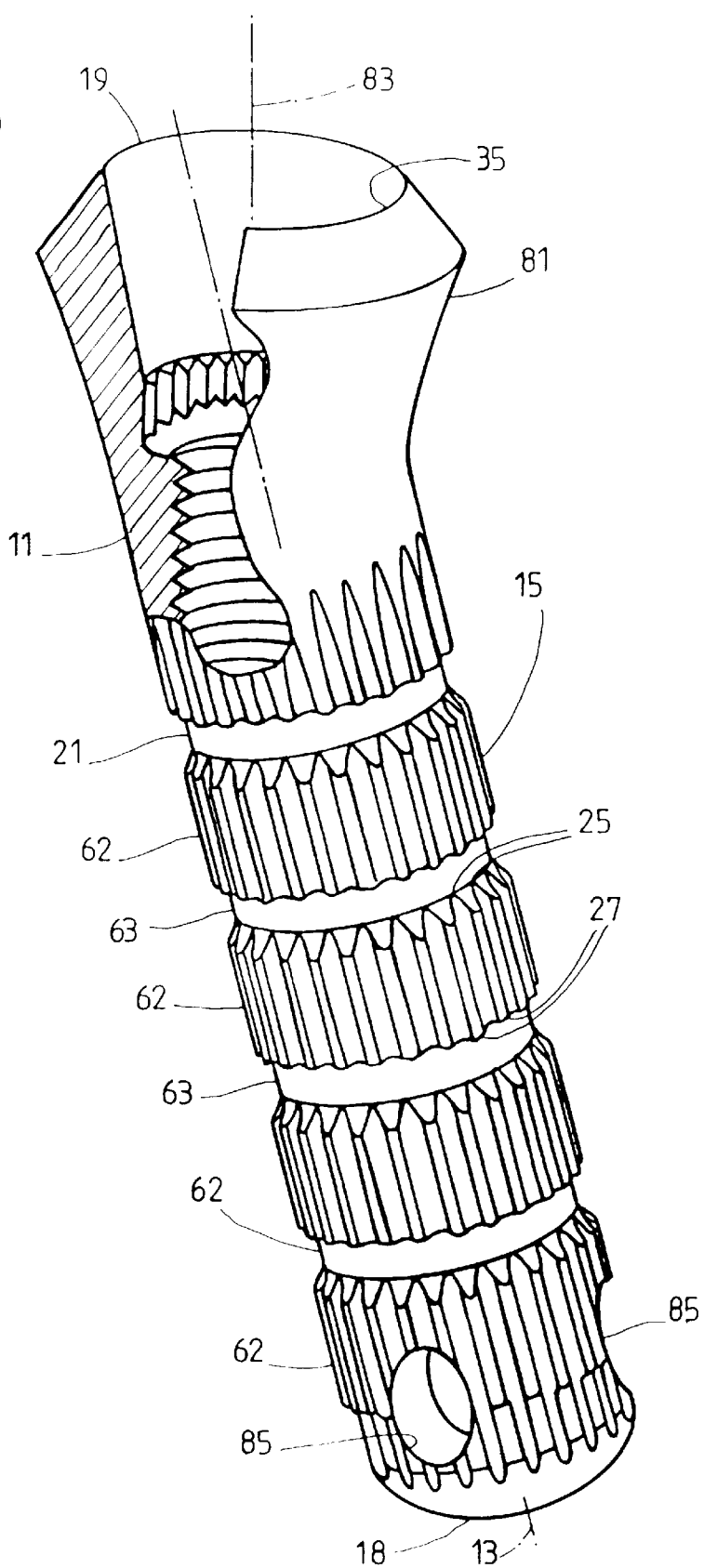

IMPLANT FOR HOLDING AND/OR FORMING A DENTAL PROSTHESIS OR ARTIFICIAL FINGER JOINT

BACKGROUND OF THE INVENTION

The invention relates to an implant for holding and/or forming a dental prosthesis or artificial finger joint.

A dental implant with an anchoring part intended to be anchored in a jaw bone is known from FIGS. 14 and 15 of U.S. Pat. No 4,447,209 A. This anchoring part has a generally cylindrical sleeve whose jacket surface is provided with axial ribs and furrows alternating along the circumference. These improve the transmission, between implant and bone, of forces directed transversely with respect to the axis of the sleeve, but they do not contribute in any appreciable way to the transmission of forces which are approximately axially parallel. The jacket of the sleeve is furthermore provided with holes. However, the many holes distributed along the entire axial extent of the implant section comprising ribs weaken the implant and increase its bending capacity. This is particularly the case if the cylindrical sleeve has only a small diameter. With such an implant, there is a considerable risk that the implant, under the effect of loads, will execute micro movements which destroy bone in the area surrounding the implant and thereby cause loosening of the implant. In addition, in the event of substantial loading, the implant can fracture at the holes located in the vicinity of the bone ridge.

An implant known from FR 2 084 522 A has a substantially conical anchoring part which, after extraction of a natural tooth, is inserted, with the thinner cone end forwards, into the freed alveolus of the jaw bone. The conical anchoring part is provided with protuberances. These are preferably inclined outward from the conical surface in the direction extending away from the thinner cone end and have a terminal surface at the end remote from the thinner end. By contrast, at their end situated nearer to the thinner cone end, they run out at least approximately to a point. Before insertion into bone, the conical anchoring parts are ground to adapt them to the individual shapes of the alveoli. This entails additional work and can also have the consequence that some of the protuberances are ground away. Because of the generally conical shape of the anchoring part, the cross-sectional shapes and cross-sectional dimensions of the protuberances in sections at right angles to the axis of the anchoring part are not constant along this axis. Accordingly, the apices, longitudinal surfaces and longitudinal edges of the protuberances are not parallel, or at least not all parallel, with the axis of the anchoring part. Moreover, the protuberances situated near the thinner cone end have smaller radial distances from the axis than do the protuberances more remote from the thinner cone end. For these reasons, upon insertion of an anchoring part into a bone, the protuberances can penetrate only with difficulty, or at most very slightly, into the bone material and they do not therefore provide stable anchoring immediately after insertion. In addition, the protuberances increase the torsional strength of the connection of the implant to the bone only slightly, even after fusion of the bone to the anchoring part. Since the protuberances have no terminal surfaces or at least no appreciable terminal surfaces at their ends situated nearer to the thinner cone end, they also contribute at most little to the transmission, from anchoring part to bone, of axially parallel pressure forces directed toward the thinner cone end.

Artificial finger joints with two pivotably connected implants or joint parts are also known. Each of these implants has an anchoring part and a joint head. When using the implant, the anchoring part is fitted in a bone of a finger. The anchoring part consists of a cylindrical pin with a smooth surface and therefore affords only a weak anchoring in the bone.

SUMMARY OF THE INVENTION

The invention is therefore based on the object of avoiding disadvantages of the known implants and of the making available an implant which, immediately after insertion into a bone, permits a stable connection to the latter. The implant according to the invention, at the latest after incorporation, into the bone or healing, can easily transmit forces to the bone, which are directed approximately transverse to the axis of the implant, and also forces which are approximately axial of the implant. The implant according to the invention is nevertheless sufficiently resistant to fracturing, even with a small diameter, and has sufficient and favorable flexural strength.

According to the invention, this object is achieved by an implant for at least one of holding and forming one of a dental prosthesis and an artificial finger joint, which includes an anchoring part for insertion into a bone that has a lower implant end, an upper implant end that is situated at least approximately level with a top of the bone when the anchoring part has been inserted into the bone, an axis, and a peripheral surface extending between the lower implant end and the upper implant end and surrounding the axis where the peripheral surface is a generally cylindrical section and has at least ten protuberances distributed around and projecting away from the axis along at least one of a helical winding and of a circle encompassing the axis. In addition, at least a majority of the protuberances are elongate in a direction parallel to said axis, and has two flanks, an apex, a protuberance end directed toward the lower implant end, and at the protuberance end, a terminal surface which forms with the axis an angle of at least 60°, and at least the apex of each protuberance is curved in a cross-section perpendicular to the axis and connects the two flanks of the respective protuberance smoothly and continuously to each other.

When the implant according to the invention is used parallel with the axis of the anchoring part, said anchoring part can be inserted into a substantially cylindrical hole of a bone in such a way that the protuberances in the cross section are pressed partially into the bone material, and accordingly bone material protrudes into the axial interspaces or furrows present between adjacent protuberances, and fills these preferably partially or, if appropriate, even completely. The bone material adjoining the anchoring part is slightly cut and/or compacted and the implant is pushed in. The compaction is particularly advantageous if the bone material adjoining the anchoring part consists partially relatively porous spongy substance. By means of the pressing-in during insertion of the implant, the anchoring part is immediately anchored in a fairly stable manner and thereby immediately acquires good stability, so-called primary stability. Upon incorporation, the bone material grows into each recess or groove present between protuberances axially spaced apart from each other. Moreover, the axial interspaces or furrows filled only partially with bone material, preferably immediately after the insertion of the implant, are filled completely with bone material upon incorporation. The implant is then anchored in a very stable manner in the bone and can transmit to the bone substantial forces approximately parallel with the axis and also substantial forces directed approximately transverse to the axis. The forces are in this case distributed fairly uniformly on a large surface area of the bone adjoining the implant. Thus, even in the event of substantial loading of the implant, it is possible to avoid excessive local stressing of the bone, which could cause absorption of bone material. The implant according to the invention can therefore also be anchored permanently.

BRIEF DESCRIPTION OF THE DRAWINGS

The subject of the invention and further advantages thereof will now be explained in greater detail with reference to illustrative embodiments represented in the drawing, in which:

FIG. 3 shows a cross section through an area of the implant according to FIGS. 1 and 2 and through a bone directly after insertion of the implant, FIG. 4 shows a representation corresponding to FIG. 3, but after the bone has fused with the implant, FIG. 5 shows a diagrammatic representation of a part of the implant and of the transmission of an approximately axial force, FIG. 6 shows a cross section through the implant according to FIGS. 1 to 5 and a diagrammatic representation of the transmission of a force directed transverse to the axis, FIG. 7 shows a representation, analogous to FIG. 6, of the force transmission for an implant without ribs and not in accordance with the invention, FIGS. 11 to 13 show representations, analogous to FIG. 5, of implants with ribs which are separated by annular grooves and have different ratios between the axial measurements of the ribs and annular grooves, FIG. 14 shows, in a developed view, a region of the peripheral surface of an implant whose ribs adjacent to each other along the periphery are axially staggered relative to each other, FIG. 15 shows an oblique view of an angled implant.

DETAILED DESCRIPTION OF THE INVENTION

As regards the illustrative embodiments described below, it should be noted that corresponding identical or similar parts of the various illustrative embodiments are in each case labeled with the same reference number.

Figure 1:
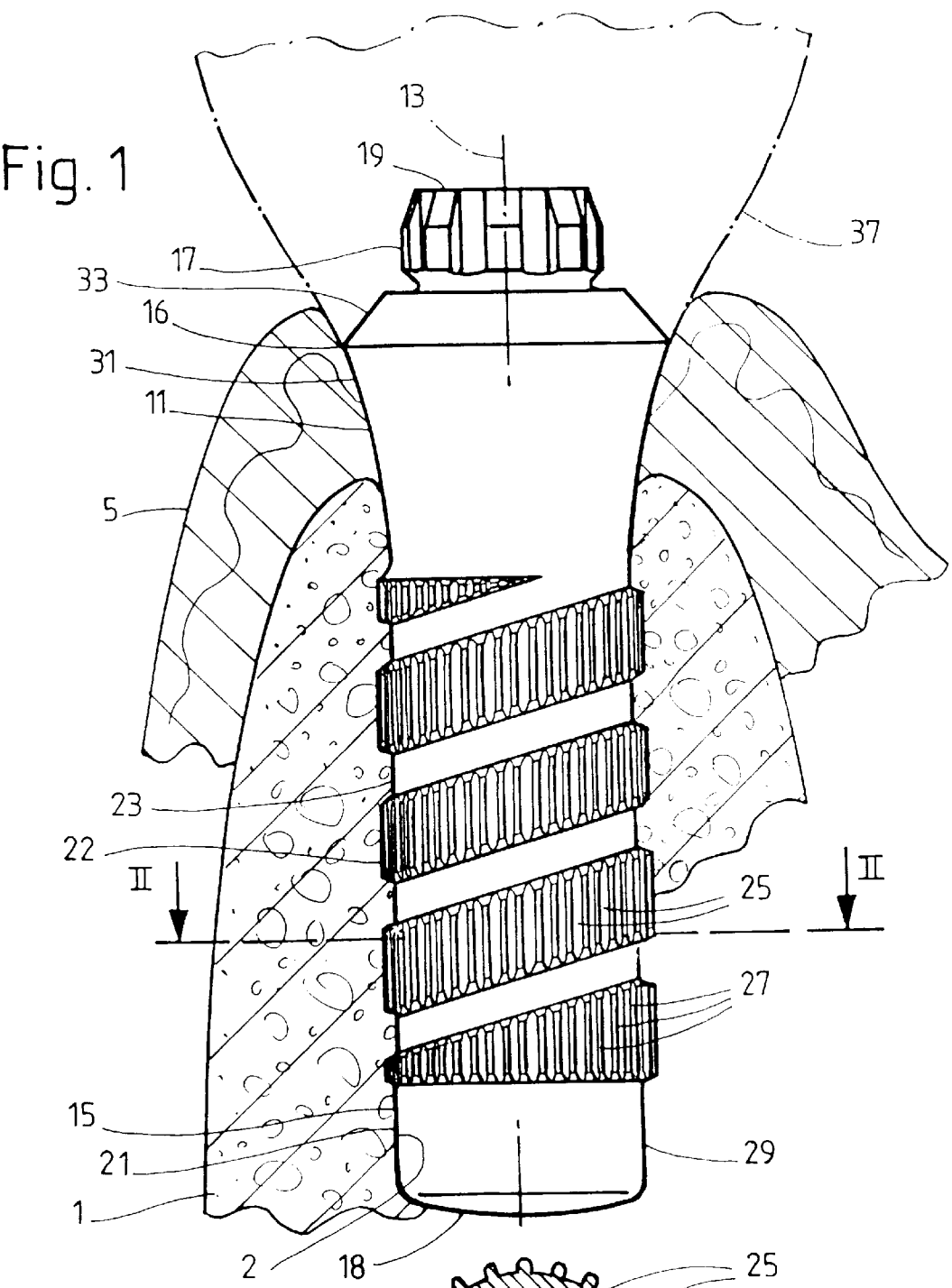
FIG. 1 shows a section through a bone and, inserted into the latter, a one-piece dental implant, in frontal view, with ribs which are separated by a helical groove.

The bone 1 which can be seen in FIG. 1 belongs for example to the lower jaw of a patient and has been provided, by means of drilling and/or reaming, with a substantially cylindrical blind hole 2 which opens into the ridge of the bone 1. FIG. 1 also shows the soft tissue 5, or gingiva, covering the bone.

A one-piece intraosseous dental implant 11, which can be seen in FIGS. 1 to 6 and is used for holding and/or forming a dental prosthesis, is elongate and generally rotationally symmetrical with respect to an axis 13. The implant has, from the bottom upward to the top, an anchoring part 15, a shoulder 16 and a head 17. The implant has two free ends directed away from each other, namely a lower, first implant end 18 formed by the anchoring part 15, and an upper, second implant end 19 formed by the head. Along most of its axial extent, the anchoring part 15 is generally cylindrical and has a peripheral surface 21. However, the generally cylindrical section of the anchoring part has a thickened area 22 or thickening 22 of helical shape. The windings of the thickened area 22 are separated from each other by a helical recess 23 or groove 23. The thickened area 22 and the groove 23 in each case have or form at least one complete winding around the axis 13, preferably at least two such windings and for example at least three such windings. The helical groove 23 has a base which is formed by a section of the peripheral surface 21. This peripheral surface section is coaxial with the axis 13 and at least partially and for example completely cylindrical. The helical area 22 has an apex parallel with the axis 13 and two edge surface or flanks directed away from each other. The helical area is delimited at the lower end and at the upper end by an edge which extends along a plane at right angles to the axis 13, so that the helical area 22 runs out to a point at both ends.

The helical thickened area 22 is divided into protuberances 27 by recesses or interspaces 25 which are distributed uniformly around the axis 13 and are parallel with the latter. The helical area 22 therefore has protuberances 27 and recesses or interspaces 25 alternating with each other around the axis 13. The recesses or interspaces 25 and the protuberances 27 are elongate, except at the running-out ends of the area 22, and formed by axial furrows 25 and ribs 27 which are axial, i.e. parallel with the axis 13. The protuberances or ribs 27 separated from each other by windings of the helical recess or groove 23 are aligned with each other in groups and form straight rows parallel with the axis 13. A complete winding of the area 22 has at least 6, preferably at least 10, still better at least 15 or at least 18, preferably at most 36 and, for example, 24 recesses or interspaces or furrows 25 distributed around the axis, and of course the same number of protuberances or ribs 27. The axial furrows 25 are, for example, approximately the same depth as the helical groove 23 or, if appropriate, slightly less deep than the latter, and they have a base which forms a strip-like section of a cylinder surface coaxial with the axis 13 or a narrow plane surface and is at least approximately smoothly contiguous with the base of the helical groove 23.

Figure 2:
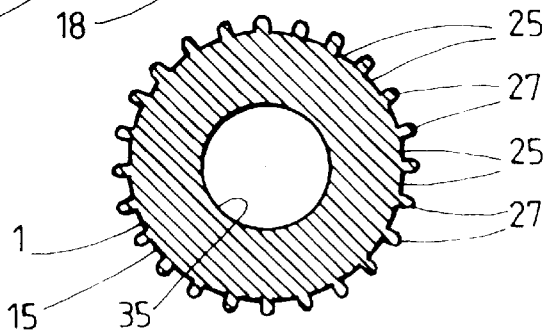
FIG. 2 shows a cross section through the implant along the line II—II in FIG. 1.

As can be seen from FIG. 2, and particularly clearly from FIGS. 3 and 4, each rib 27 has two plane flanks parallel with the axis 13 and with each other, and an apex which is convexly curved in cross section and which smoothly and continuously connects the two flanks to each other. According to FIGS. 2 to 4, for example, more or less sharp edges are present between the flanks of the ribs and the base surfaces of the furrows 25. However, these sharp edges could be replaced by curved transitions continuously connecting the flanks of the ribs and the base surfaces of the furrows to each other. The apices, flanks and longitudinal edges of the ribs are straight and parallel with the axis 13. The apices or, to be more exact, the apical lines present at the highest points of the ribs together define a common cylinder surface for all the ribs. The apical lines of all the ribs accordingly have the same radial distance from the axis 13.

Each rib 27 has two terminal surfaces which are directed away from each other and which are formed by the two edge surfaces or flanks of the helical area 22. Those terminal surfaces of the ribs situated nearer to the first implant end 18 are straight in sections parallel with the axis 13 and in these sections form with the axis 13 an angle which is labeled α in FIG. 5. At least in that section of the area 22 in which the lower edge of the area 22 is contiguous with the groove 23 and is helical, these terminal surfaces are inclined in axial section outward from the axis 13 away from the first implant end. At least in said section of the area 22, the angle α is preferably at least 60° and for example approximately 70° to 80°. Those terminal surfaces of the ribs 27 directed away from the first implant end 18 are, for example at least in that section of the area 22 in which the last-mentioned terminal surfaces are contiguous with the helical groove 23, likewise straight in axial sections and inclined outward from the axis toward the first implant end 18, forming with the axis an angle which, for example, is the same as the angle α. Each terminal surface of a rib is delimited from the or each longitudinal surface of the rib by, for example, a moderately sharp edge. In cross sections at right angles to the axis 13, the ribs 27 have constant cross-sectional dimensions essentially along their entire length, namely from one inclined terminal surface to the opposite inclined terminal surface. Moreover, all the ribs have the same cross-sectional shapes and the same cross-sectional dimensions.

The pitch of the helical area 22 is designated by s in FIG. 5 and in the case of a dental implant is preferably 1 mm to 3 mm and for example 1.5 mm to 2.5 mm. In the main section of the area 22 delimited at the top and bottom by a helical edge, said area 22 and its ribs 27 have a length or axial dimension a. The helical groove 23 has, in axial sections, a dimension (or axial width) b measured in the axial direction. As the ribs 27 have inclined terminal surfaces, the dimensions a and b are measured at half the height of the ribs 27. The length or axial dimension a of the ribs is at least 20%, preferably at least 50%, and still better more than 50% of the pitch s, namely for example 60% to 80% of the pitch s. The dimension b of the groove 23 is of course equal to the difference s−a. If the dimension a of the thickened area 22 and of the ribs 27 is more than 50% of the pitch s, the dimension a is accordingly greater than the dimension b of the groove measured in the axial section. The cylindrical enveloping surface hugging the apices of the ribs 27 has a radius which is designated by $R_a$ in FIG. 3. The base surfaces of the axial furrows 25 define a cylinder surface with a radius $R_i$. The radially measured depth of the helical groove 23 and of the axial furrows 25 and the radial heights of the ribs 27 are for example 0.15 mm to 0.5 mm and for example at least 10% and at most 35% of the radius $R_a$. That section of the anchoring part extending from the lower end to the upper end of the helical area 22 has a surface which, as a result of the groove 23 and the furrows 25, is at least 30% and for example approximately or at least 50% greater than a cylindrical enveloping surface hugging the apices of the ribs and extending over the axial dimension of the thickened area 22.

Between the first, lower implant end 18 and the lower end of the thickened area 22 situated nearer to the latter, the peripheral surface of the anchoring part 15 still has for example a smooth cylindrical end section 29 having the same diameter as the base surface of the helical groove. Above the thickened area 22, the implant has a section 31 which widens in a trumpet shape upward to the shoulder 16 and which, at the upper end of the groove 23, is continuous with the base thereof. The shoulder 16 has a conical shoulder surface 33 tapering toward the head 17. The implant also has an axial blind hole 35 which opens into the second implant end 19 formed by the head 17 and which has for example a section with an internal thread. The implant 11 and in particular its anchoring part 15 are free from radial holes or from holes otherwise approximately transverse to the axis 13.

The implant is made of a metal, for example titanium. That area of the peripheral surface 21 extending from the first implant end 18 to the upper end of the thickened area 22, and the terminal surface of the implant present at the first implant end 18, can be roughened by chemical treatment or can be provided with a rough, sprayed-on titanium coating, and then have fine pores lying in a microscopic range.

To insert the implant 11 into the bone 1, the latter is provided with the blind hole 2 already mentioned. This hole is drilled and/or reamed in such a way that it has a radius $R_m$ which is smaller than the radius $R_a$ and at least equal to the radius $R_i$ and preferably greater than the latter. A dentist can then push the anchoring part 15 into the hole 2, parallel with the axis of the hole 2 and with the axis 13 of the implant coincident with said axis. In doing so, the terminal surfaces of the ribs 27 of the lowermost winding of the thickening 22, situated nearer to the first implant end 18, can cut slightly into the bone material so that axial furrows are obtained in the previously cylindrical boundary face of the blind hole 2 in the bone 1. The bone material at the ribs is also pressed radially outward and compacted somewhat. Upon insertion of the implant into the bone, the outer sections of the ribs 27 thus penetrate into the bone material in accordance with FIG. 3. After the implant has been inserted, the first implant end 18 thereof forms the deepest point of the implant in the bone. The whole area 22 is also situated within the bone. After the implant has been inserted, the bone material fills the outer areas of the furrows 25. The implant is thus immediately anchored in a stable manner in the bone upon insertion and thus has a good primary stability. In addition, the slight compression of the bone which occurs in places as the implant is pushed in also promotes growth of bone material.

According to FIG. 1, the implant 11 is inserted through the gum, so that it protrudes from the bone 1 and passes through the soft tissue 5, i.e. the gingiva. The upper, second implant end 19 situated above the bone is then closed off in conventional manner with an incorporation cap, so that the implant can become incorporated in the bone. The bone grows into the helical groove 23 and, according to FIG. 4, into the axial furrows 25, so that the bone material completely fills the groove 23 and the furrows 25 after a phase of incorporation lasting for example about 3 months. Once the implant has become incorporated in the bone, the incorporation cap is removed and an abutment element 37 or superstructure, indicated by dot-and-dash lines in FIG. 1, is fitted onto the implant 1 and secured in the blind hole 35. The abutment element or superstructure can consist, for example, of a crown for an individual tooth or of at least part of a bridge or at least part of a tooth prosthesis having several prosthetic teeth and it then forms together with the implant, or possibly together with other implants, a dental prosthesis.

When a patient chews with the dental prosthesis held and/or formed by the implant, forces which inter alia are more or less parallel with the axis 13 are exerted on the implant 11. In FIG. 5, such an axial force $F_z$, namely a compression force directed toward the first implant end 18, is represented by an arrow or vector. This force $F_z$ is transmitted to the bone 1 from the anchoring part 15 of the implant 11 and in the process is divided into subsidiary forces. These include in particular subsidiary forces $F_{z,1}$ transmitted to the bone at the lower terminal surfaces of the protuberances or ribs 27, and subsidiary forces $F_{z,2}$ transmitted to the bone at the first implant end. The inclination of the lower terminal surfaces of the ribs contributes in this case to a favorable introduction of the subsidiary forces $F_{z,1}$ into the bone.

During chewing, forces or force components directed approximately transverse to the axis 13 are also exerted on the implant. Such a force $F_x$ directed transverse to the axis 13 is represented in FIG. 6 by an arrow or vector. The force $F_x$ is transmitted from the anchoring part 15 to the bone and likewise broken down into subsidiary forces. In particular, a subsidiary force $F_{x,1}$ is transmitted to the bone from each rib 27. Upon transmission to the bone, the force $F_x$ is therefore distributed relatively uniformly over a diameter or semi-circle at right angles to the direction of force. Since the terminal surfaces of the ribs extend along a helical line and, viewed in the radial direction, are inclined toward a plane perpendicular to the axis 13, the terminal surfaces of the ribs can also transmit, to the bone, forces which are directed transverse to the axis 13.

Thus, axial forces or force components, and forces or force components directed transverse to the axis 13, and accordingly forces with any desired directions, are distributed relatively uniformly to large surfaces of the bone adjoining the implant and transmitted to said bone. Even when substantial forces are to be transmitted, this ensures that neither absorption of bone material nor loosening of the implant takes place. If a torque is exerted on the implant relative to the axis 13, the ribs 27 and their terminal surfaces extending along a helical line increase the resistance of the implant to twisting about the axis 13 and thus increase the torsional strength of the anchoring.

Opposite each section of the helical groove 23 is a section of the thickened helical area 22. As has been mentioned, the dimension a of the ribs 27 and of the area 22 is also greater than the dimension b of the groove 23. The groove 23 does not therefore cause any appreciable weakening of the anchoring part. Since the implant 1 and in particular its anchoring part also have no holes extending transverse to the axis 13, the implant has a high degree of strength and bending stiffness, even when the anchoring part has a small diameter.

The anchoring part of the implant represented in FIG. 7, and not in accordance with the invention, has no furrows and ribs corresponding to the furrows 25 and ribs 27, but only a smooth cylinder surface. If a force $F_x$ perpendicular to the axis of the anchoring part impacts on such an implant, said force is broken down into subsidiary forces $F_{x,2}$ which vary greatly over a diameter perpendicular to the direction of the force $F_x$. Moreover, the force $F_x$ is distributed on a smaller surface than in the case of an implant according to the invention with the same diameter of the anchoring part. Furthermore, in the case of an implant not in accordance with the invention, and having an anchoring part with a smooth cylinder surface, axial forces are of course also distributed on a smaller surface than in an implant according to the invention whose anchoring part has the same diameter.

After the process of healing, the bone 1 and the soft tissue 5, above the thickened area 22 having ribs and furrows, mold onto the smooth peripheral surface, rotationally symmetrical with the axis 13, of the trumpet-shaped section 31 of the implant according to the invention. The soft tissue can also mold onto the abutment element 37. This guarantees an effective, tight closure of the hole in the bone. This at least substantially prevents microorganisms from penetrating between the soft tissue 5 and the implant 11 and into the hold 2 of the bone 1.

Figure 8:
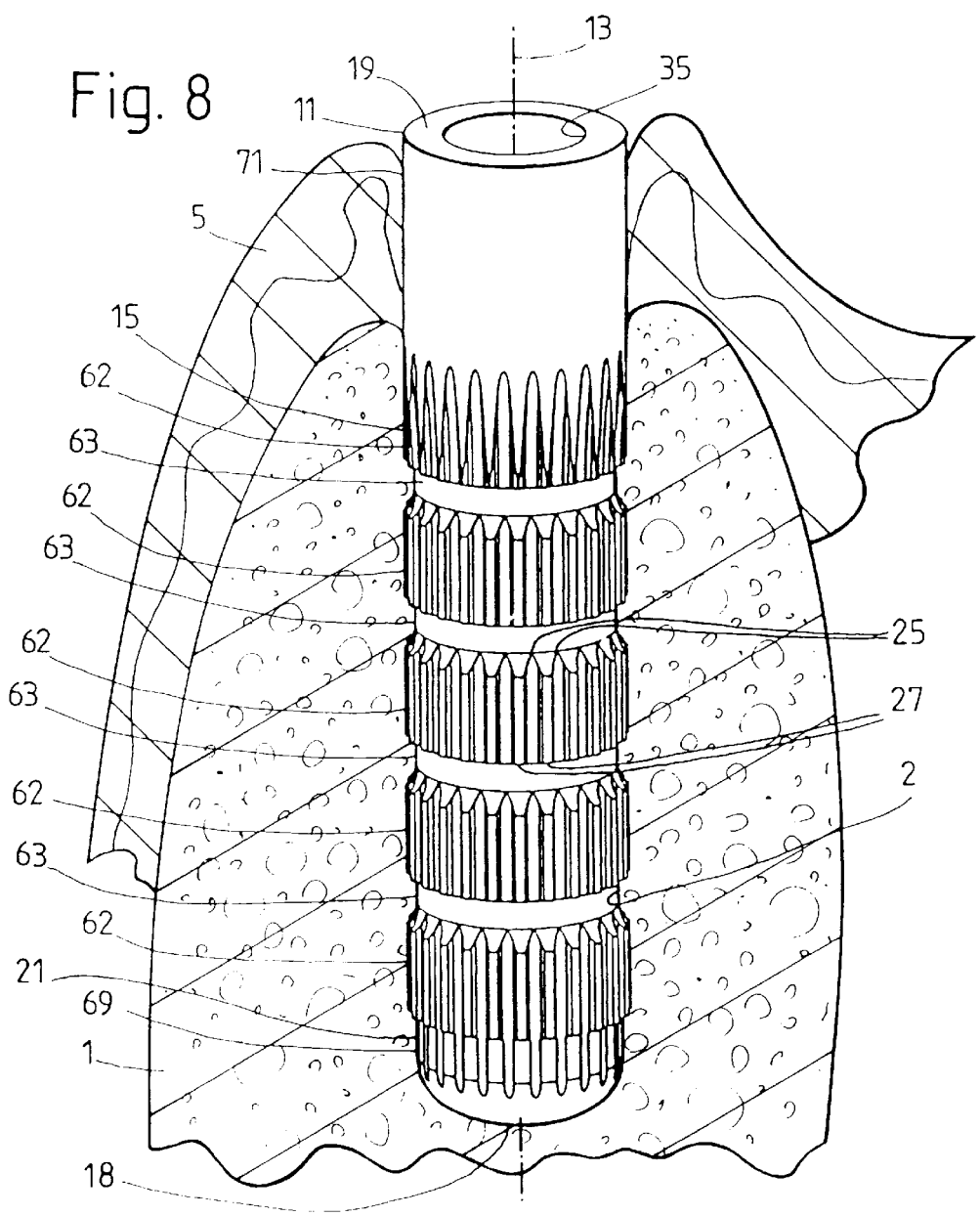
FIG. 8 shows an oblique view of a generally completely cylindrical implant which has been inserted transgingivally into a bone and whose ribs are separated from each other by annular grooves.
Figure 9:
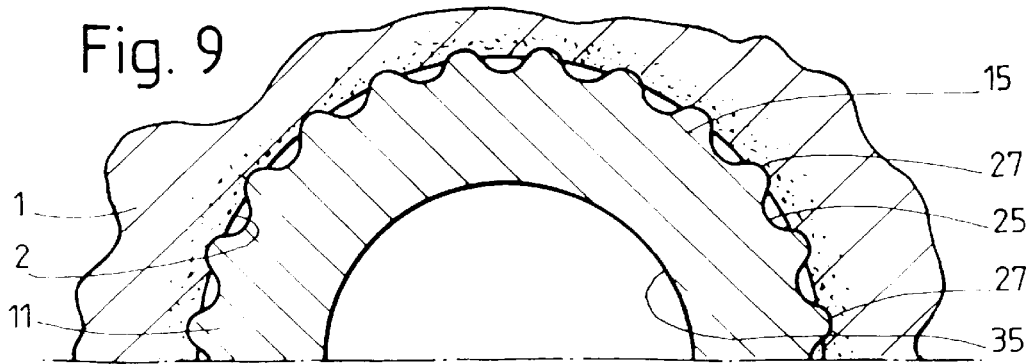
FIG. 9 shows a cross section through the implant according to FIG. 8 on a larger scale, directly after insertion of the implant into the bone.

A bone 1, soft tissue 5 and a dental implant 11 with an axis 13 can be seen in FIGS. 8 and 9. In this variant, the whole implant is generally cylindrical. The peripheral surface 21 of the anchoring part 15 anchored in the hole 2 of the bone 1 after insertion of the implant has at least two annular areas 62 which surround the axis and are separated from each other by an annular recess 63, i.e. an annular groove 63. The areas 62 are divided into protuberances 27 by recesses or interspaces 25 distributed around the axis 13. At least three, and still better at least four, for example five, such annular areas 62 are preferably present, separated from each other by annular grooves 63 and spaced apart from each other in the axial direction. Accordingly, at least two annular grooves 63 are then present. The interspaces 25 and protuberances 27 are again elongate and form furrows 25 and ribs 27 parallel with the axis 13. Each area 62 thus forms a circular collar of furrows 25 and ribs 27 alternating successively around the axis 13. According to FIG. 9, the base surfaces of the furrows 25 and the apices of the ribs 27 are curved in cross section in such a way that they smoothly and continuously connect the flanks of the ribs to each other.

The depths of the axial furrows 25 are identical to the depths of the annular grooves 63 or slightly smaller than these. The base surfaces of the annular grooves 63 are formed by smooth cylinder surfaces.

Between the lower, first implant end 18 and the lowermost thickened area 62, or in the lower part thereof, the anchoring part has a generally cylindrical end section 69. The diameter of the latter is smaller than that of the enveloping surface defined by the rib apices, but greater than the diameter of the cylinder surface which is defined by the deepest sites of the ribs 25. The end section 69 is divided by the furrows of the lowermost thickening, or continuations of these furrows, likewise into rib-shaped protuberances, which are however distinctly lower than the ribs situated further up. The furrows and ribs of the end section 69 extend as far as the, in axial section, slightly convexly curved terminal surface at the first implant end 18. Above the topmost annular area 62 comprising axial ribs and furrows, the implant has an end section 71 with a smooth cylindrical peripheral surface extending as far as the second implant end 19. The diameter of said peripheral surface is equal to the diameter of the cylindrical enveloping surface hugging the apices of the axial ribs 27. The peripheral surface of the end section 71 thus merges smoothly with the highest parts of the ribs. The annular areas 62 can be regarded as areas of thickening in relation to the annular grooves 63.

In the implant designed according to FIGS. 8 and 9, therefore, at least all those protuberances or ribs 27 situated along the axis between other ribs of the same row of ribs, and thus belonging neither to the lowermost nor to the topmost collar of ribs, have constant and, for all the ribs, identical cross-sectional shapes and cross-sectional dimensions along their entire length.

With the exception of the ribs belonging to the topmost area 62, the ribs 27 have, at both ends, terminal surfaces forming an angle with the axis 13. The ribs of the topmost area 62 only have terminal surfaces at their lower end. For this reason, the furrows of the topmost area 62 form, at their upper ends, outwardly tapering terminal surfaces forming an angle with the axis. Otherwise, the implant represented in FIGS. 8 and 9, like the implant represented in FIGS. 1 to 6, has no holes extending transverse to the axis.

According to FIG. 8, the implant is inserted into the hole 2 in the bone 1 in such a way that the topmost area 62 having furrows and ribs is situated slightly below the ridge of the bone 1. The length of the end section 71 having a smooth cylindrical peripheral surface is dimensioned such that the upper, second implant end 19 is situated approximately level with the ridge of soft tissue 5. Otherwise, the implant once again has an axial blind hole 35 which opens into the upper, second implant end 19 and is there surrounded by a plane annular surface.

Figure 10:
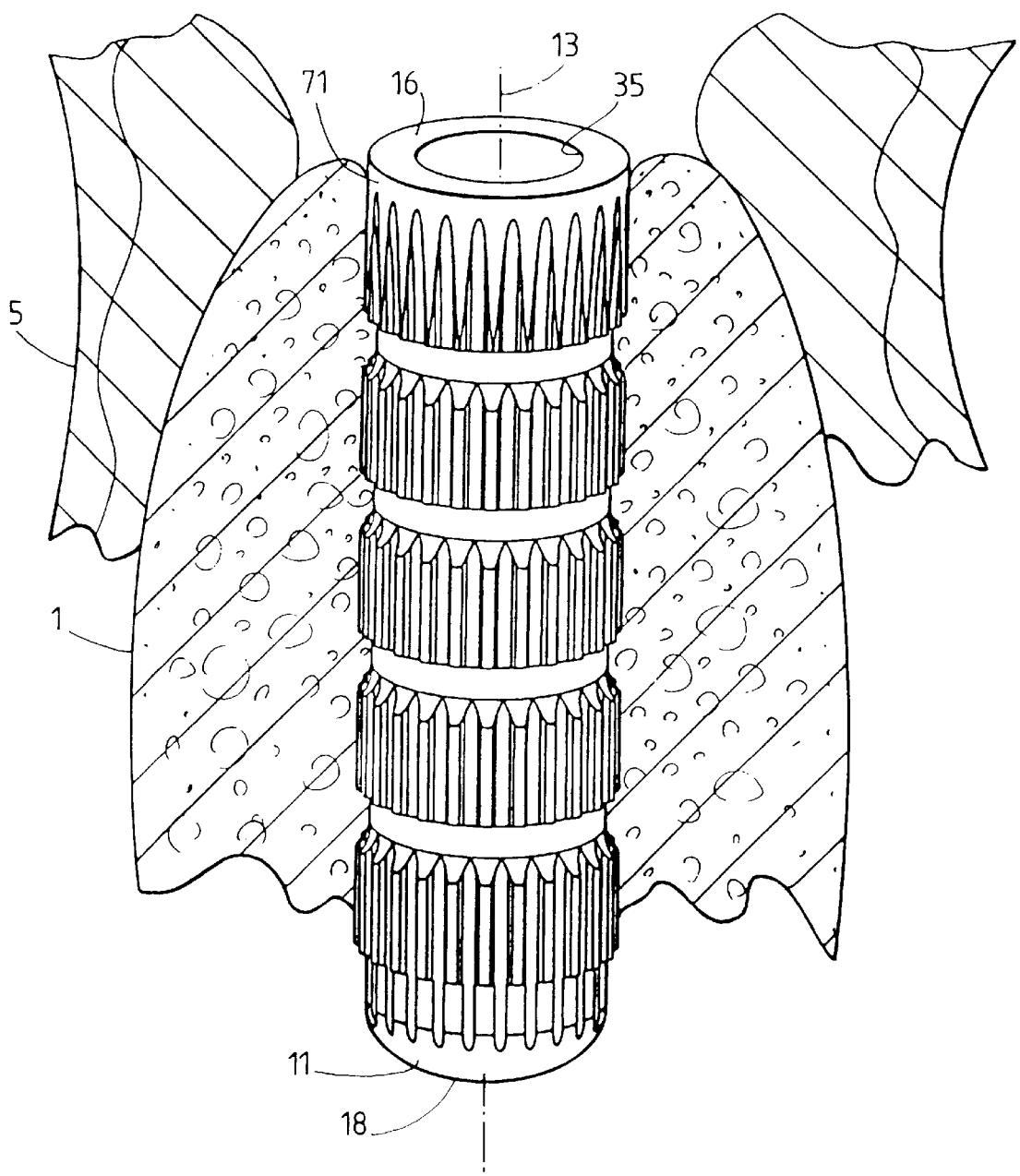
FIG. 10 shows an oblique view of another generally completely cylindrical implant which has been inserted subgingivally into a bone.

The implant 1 shown in FIG. 10 is substantially of the same design as the implant represented in FIGS. 8 and 9 and differs from the latter only in that the end section 71 with a smooth, cylindrical peripheral surface is only very short. The implant 11 represented in FIG. 10 is inserted subgingivally into the bone 1 in the mouth of a patient. The first implant end 18 is once again situated at the deepest point in the bone 1, while the second implant end 19 is situated approximately level with the bone ridge and/or only slightly above the bone. The implant is then completely covered by soft tissue during the incorporation phase.

FIGS. 11 to 13 show areas of the anchoring parts 15 of various implants 11. These anchoring parts 15 are of similar design to those of the implants represented in FIGS. 8 to 10 and in particular have annular areas 62 and, arranged between these, annular grooves 63. The areas 62 once again have axial furrows 25 and ribs 27. The implants 11 represented in FIGS. 11 to 13 differ from the implants according to FIGS. 8 to 10 in that, like the implant shown in FIG. 1, they have, between the first implant end 18 and the area 62 having furrows and ribs which is situated nearest to this, an end section 29 with a completely smooth cylinder surface. The lower terminal surfaces of the ribs 27 of the implants represented in FIGS. 11 to 13 form, in axial sections with the axis 13, an angle α which, as in the case also of the implants according to FIGS. 8 to 10, lies approximately in the same range as in the implant described with reference to FIGS. 1 to 5. In the implants represented in FIGS. 11 to 13, and for example also in the implants according to FIGS. 8 to 10, the upper terminal surfaces of the ribs have a conical section, therefore straight in axial sections, which is continuously connected to the cylindrical base surface of the contiguous annular grooves 63 via a transition section which is concavely curved in axial sections.

In FIGS. 11 to 13, the distances u between corresponding points of two annular areas 62 succeeding each other along the axis are also indicated. The distance u corresponds more or less to the pitch s of the helical area 22 of the implant first described. Moreover, FIGS. 11 to 13 show the axial dimensions a or lengths of the annular areas 62 and ribs 27, and the axial dimensions b of the annular grooves 63. The dimensions a, b are in this case measured at half the height of the ribs, in the same way as with the implant first described. The distance u corresponding to the pitch of a thread is preferably at least 1 mm, preferably at most 5 mm, and for example 1.5 mm to 2.5 mm or up to 3 mm. The axial dimension a or length of the ribs can be approximately 20% to 80% of the distance u and can be smaller or greater than the dimension b or approximately the same as this. FIGS. 11 to 13 show a number of different possibilities for dimensioning the distance u and the distances a, b for a given diameter of the anchoring part.

In FIG. 14, part of an implant 11 is represented in an enlarged view. The implant has an anchoring part 15 with a generally cylindrical peripheral surface 21. The latter has elongate rib-like protuberances 27 with a longitudinal direction parallel with the axis 13. The protuberances 27 or ribs are arranged in straight row parallel with the axis. Recesses 23 are present between the protuberances 27 belonging to the same row. The protuberances belonging to adjacent rows are mutually staggered parallel with the axis 13. The upper end of one protuberance 27 protrudes between two protuberances of the two adjacent rows of protuberances. The lower end of the protuberance likewise protrudes between two protuberances of the two adjacent row. Between the protuberances of two adjacent rows there are recesses or interspaces 25 which together form a furrow parallel with the axis 13. At the two ends of a protuberance 27 there are terminal surfaces inclined away from the base of the recesses 23 toward the center of the protuberance.

The dental implant shown in FIG. 15 is angled and has a generally cylindrical anchoring part 15 coaxial with the axis 13. This anchoring part 15 forms the first implant end 18 and has a peripheral surface 21. The implant has an end section 81 which adjoins the upper end of the anchoring part 15 and which forms the second implant end 19 and is substantially coaxial with an axis 83 which forms an angle with the axis 13. The blind hole 35 opening into the second implant end 19 is coaxial with the axis 83 and has inter alia a section with an internal thread.

As in the implants according to FIGS. 8 to 13, the anchoring part 15 has annular areas 62 which are separated from each other by annular grooves 63 and have furrows 25 and ribs 27 alternating with each other along the periphery and parallel with the axis 13. In the lower area of the anchoring part 15, the implant has a blind hole which is coaxial with the axis 13 and opens into the first implant end 18. Also, near the first implant end, the implant has at least one hole 85 which is transverse and radial with respect to the axis 13 and opens into the last-mentioned blind hole, there being for example at least two holes 85 distributed around the axis 13. The holes 85 can for example pass through the lowermost annular area 62 having furrows and ribs.

In the same way as with the straight implants described above, the anchoring part 15 of the angled implant can be pushed into a hole in a bone parallel with the axis 13. In the phase of incorporation, the bone can then also grow through the holes 85 and into the blind hole opening into the first implant end 18. Anchoring is further improved by this means.

However, in order to ensure that the implant is not excessively weakened by holes extending transverse to the axis 13, only a small number of such holes should be present. Moreover, at least approximately the third of the anchoring part farthest from the first implant end should preferably be free from holes extending transverse to the axis 13. In addition, the anchoring part should preferably have at least one annular area 62 and still better at least two annular areas 62 in which the peripheral surface 21 is compact and free from holes.

Holes extending transverse to the axis 13 could also be provided in an implant designed substantially in accordance with FIG. 1 and having a helical area 22. However, such holes should then likewise only be present in the lower part of the implant, so that the helical area 22 has at least one complete helical winding and better still at least two complete helical windings in which the peripheral surface 21 is compact and free from holes. The same applies to an implant with protuberances arranged in accordance with FIG. 14.

Figure 16:
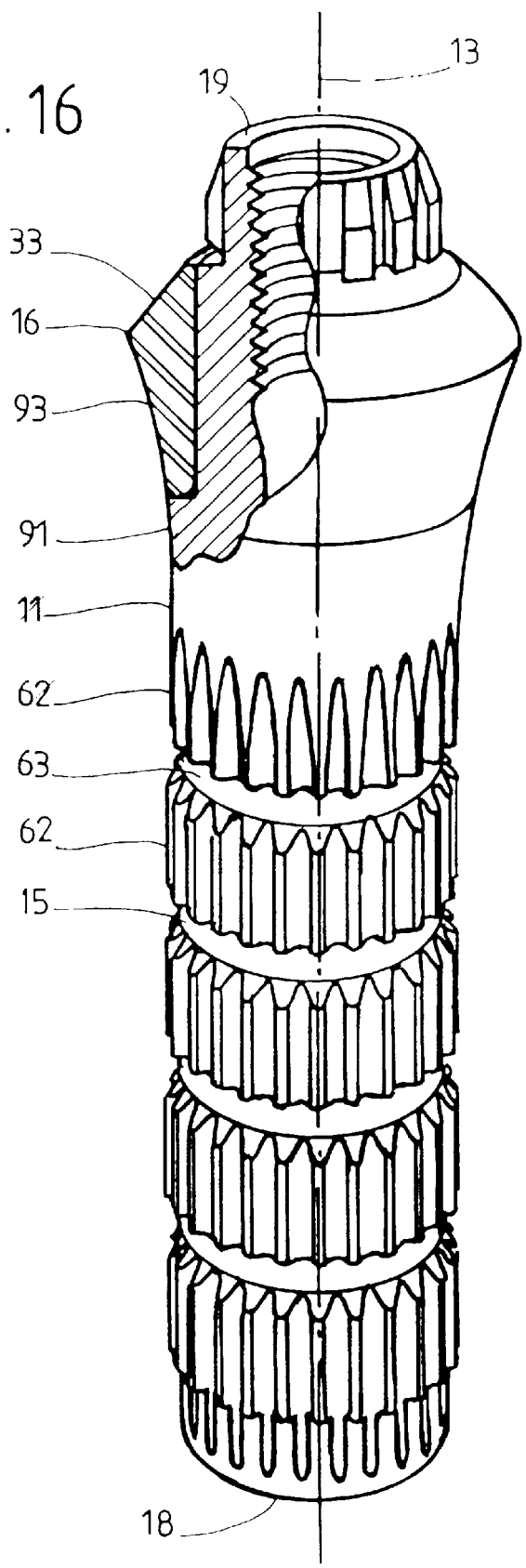
FIG. 16 shows an oblique view of an implant with a metal main body and a ceramic ring.

The implant 11 shown in FIG. 16 has a similar external shape to the implant according to FIG. 1. However, instead of having a helical area, the anchoring part 15 has a plurality of annular areas 62 which are separated from each other by annular grooves 63 and have axial furrows and ribs. The implant shown in FIG. 16 has a one-piece main body 91 which is made of metal, namely titanium, and extends from the first implant end 18 to the second implant end 19. The implant moreover has an annular ceramic body 93 which forms the shoulder 16 with the annular shoulder surface 33. The ceramic body 93 sits in an annular neck of the metal main body and is connected to the main body rigidly and substantially nonreleasably, for example by means of an adhesive connection or solder connection.

Figure 17:
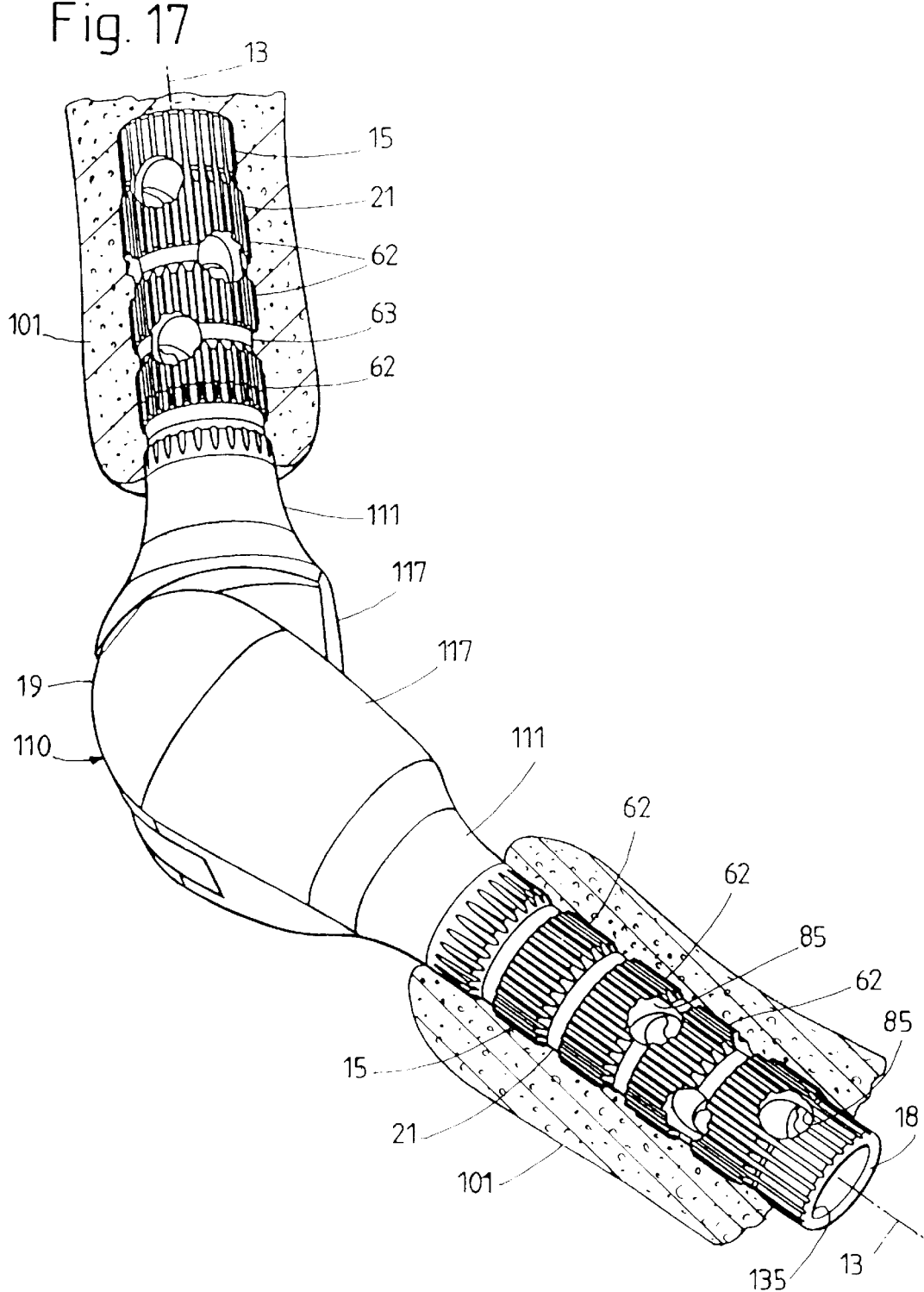
FIG. 17 shows an oblique view of an artificial finger joint with two implants inserted into bones.

FIG. 17 shows two bones 101 of a finger of a patient and an artificial finger joint 110. The finger joint 110 has two implants 111. Each implant 111 has an anchoring part 15 and a joint part or joint head 117. Each anchoring part has a generally cylindrical peripheral surface 21. The latter has, for example, a number of annular areas 62 which are separated from each other by annular grooves 63 and are provided with axial furrows 25 and ribs 27. Each anchoring part 15 has an axial hole 135 which opens into the first implant end 18 formed by the anchoring part. The second implant end 19 is formed by the joint part 117. Each anchoring part is formed by a metal sleeve, for example of titanium, with a continuous axial hole. The two joint parts are made of a slightly elastically deformable plastic, have swivel bearing means which can be clipped into each other, and are connected rigidly to the anchoring part belonging to the relevant implant. Each anchoring part also has a number of holes 85 extending transverse to the axis 13 and opening into the axial hole 135.

Unless otherwise stated in the descriptions of FIGS. 8 to 16, the implants represented in said figures can have similar properties to an implant or the implant previously described.

In addition, features of different implants can be combined with each other. For example, the annular areas 62 of the implants represented in FIGS. 8, 10, and 15 to 17 could be replaced by a helical area 22. In addition, the upper terminal surface of the helical area 22 shown in FIG. 1 can, like the upper terminal surfaces of the annular areas 62 in FIGS. 11 to 13, be partially straight and partially concavely curved in axial section. Moreover, an anchoring part could also be provided which has more than one helical area 22 and more than one helical groove, for example two or three such areas and grooves, and which is designed analogous to a multi-start thread.

What is claimed is:

1. An implant for at least one of holding and forming one of a dental prosthesis and an artificial finger joint, said implant including an anchoring part for insertion into a bone comprising:
    a lower implant end that is inserted into the bone;
    an upper implant end that is situated at least approximately level with a top of the bone when the anchoring part has been inserted into the bone;
    an axis; and
    a peripheral surface extending between said lower implant end and said upper implant end and surrounding said axis, said peripheral surface being a generally cylindrical section and having at least about ten protuberances distributed thereon around and projecting away from said axis along at least one of a helical winding and of a circle encompassing said axis,
    wherein at least a majority of the protuberances are elongate in a direction parallel to said axis forming a length, and have two flanks, an apex, a protuberance end directed toward said lower implant end, and, at said protuberance end, a terminal surface which forms with said axis an angle of at least 60°, and
    wherein at least the apex of each protuberance is curved in a cross-section perpendicular to the axis and connects the two flanks of the respective protuberance smoothly and continuously to each other.

2. The implant according to claim 1, wherein at least a majority of the protuberances have a constant cross-sectional shape and a constant cross-sectional size at least over most of the length of protuberances.

3. The implant according to claim 1, wherein the at least ten protuberances form rows distributed around the axis and parallel with it with adjacent protuberances belonging to the same row being separated by a recess and wherein at least all of the protuberances belonging to the same row and situated between other protuberances of this row have identical cross-sectional dimensions and identical cross-sectional shapes.

4. The implant according to claim 1, wherein the helical winding of at least ten protuberances is separated by at least one helical recess extending around said axis thereby providing space between terminal surfaces of certain protuberances.

5. The implant according to claim 4, wherein only one helical recess is provided, said helical recess having a pitch (s) and wherein at least those protuberances which are disposed between windings of the helical recess have an axial dimension which is at least 50% of the pitch (s).

6. The implant according to claim 5, wherein the helical recess forms at least two complete windings.

7. The implant according to claim 5, wherein the helical recess forms at least three complete windings.

8. The implant according to claim 1, wherein the at least ten protuberances are distributed along a circle encompassing said axis, and are divided into at least two rows separated from each other by at least one annular recess extending around the axis.

9. The implant according to claim 1, wherein groups of the at least ten protuberances are arranged in rows parallel with said axis, said rows of protuberances being mutually staggered in the axial direction so that a protuberance in a row is positioned between protuberances in an adjacent row.

10. The implant according to claim 1, wherein each flank of a protuberance forms a plane that is parallel to said axis.

11. The implant according to claim 1, wherein the at least ten protuberances following one another along one of a helical winding and a circle around the axis are separated by interspaces, the interspaces having a base surface curved in a cross-section perpendicular to said axis in such a way that the interspaces smoothly and continuously connect the flanks of adjacent protuberances to each other.

12. The implant according to claim 1, wherein at least about fifteen protuberances are distributed along at least one of helical winding and of a circle encompassing the axis.

13. The implant according to claim 1, wherein a portion of said peripheral surface on which the protuberances are disposed has a surface area that is at least 30% greater than that of a cylindrical enveloping surface, which extends along the axial extent of said portion and hugs the apices of the protuberances.

14. The implant according to claim 1, wherein a portion of said peripheral surface on which the protuberances are disposed has a surface area that is at least 50% greater than a cylindrical enveloping surface, which extends along the axial extent of said portion and hugs the apices of the protuberances.

15. The implant according to claim 1, wherein the anchoring part is a one-piece body.

16. The implant according to claim 1, wherein said terminal surfaces of at least the majority of the protuberances are inclined away from said axis and from said lower implant end.

17. An implant for at least one of holding and forming one of a dental prosthesis and an artificial finger joint, said implant including an anchoring part for insertion into a bone comprising:

a lower implant end that is inserted into the bone;

an upper implant end that is situated at least approximately level with a top of the bone when the anchoring part has been inserted into the bone;

an axis; and a peripheral surface extending between said lower implant end and said upper implant end and surrounding said axis, said peripheral surface being a generally cylindrical section and having a plurality of protuberances distributed thereon around said axis and projecting away from said axis, wherein at least the section of the anchoring part having the protuberances and the peripheral surface consists over its entire cross-section, all around said axis and along the entire axial extension of this section of a one-piece body, wherein at least a majority of the protuberances are elongate in a direction parallel to the axis and have two flanks, an apex parallel with said axis, a protuberance end directed toward said lower implant end, and, at the protuberance end, a terminal surface which forms with the axis an angle of at least 60°, wherein said plurality of protuberances are arranged in at least about ten rows of protuberances, each protuberance row being concentric with respect to said axis and comprising at least two axially aligned protuberances, and axially adjacent protuberances belonging to the same row are separated by a recess from one another, wherein at least the apex of each protuberance is curved in a cross-section perpendicular to the axis and connects the two flanks of the respective protuberance smoothly and continuously to each other, and wherein a portion of said peripheral surface on which the protuberances are disposed has a surface area that is at least 30% greater than that of a cylindrical enveloping surface, which extends along the axial extent of said portion and hugs the apices of the protuberances.

18. The implant according to claim 17, wherein protuberances belonging to the same row are separated from each other by one of a helical recess and of at least one annular recess.

19. The implant according to claim 17, wherein said terminal surfaces of at least the majority of the protuberances are inclined away from said axis and from said lower implant end.

20. An implant for at least one of holding and forming one of a dental prosthesis and an artificial finger joint, said implant including an anchoring part for insertion into a bone comprising:

a lower implant end that is inserted into the bone;

an upper implant end that is situated at lest approximately level with a top of the bone when the anchoring part has been inserted into the bone;

an axis; and a peripheral surface extending between said lower implant end and said upper implant end and surrounding said axis, said peripheral surface being a generally cylindrical section and having a plurality of protuberances distributed thereon around said axis and projecting away from said axis, wherein at least the section of the anchoring part having the protuberances and said peripheral surface consists of a one-piece body, over its entire cross-section, all around said axis and along the entire axial extension of this section, wherein at least a majority of the protuberances are elongate in a direction parallel to the axis and have two flanks, an apex parallel with said axis, a protuberance end directed toward said lower implant end, and, at the protuberance end, a terminal surface which forms with the axis an angle of at least 60°, said terminal surfaces of at least the majority of the protuberances being inclined away from said axis and from said lower implant end, wherein said plurality of protuberances are arranged in at least about ten circular windings of protuberances, each protuberance, circular winding being concentric with respect to said axis, comprising at least two axially aligned protuberances, and separated by a helical recess from an adjacent circular winding, wherein at least the apex of each protuberance is curved in a cross-section perpendicular to the axis and connects the two flanks of the respective protuberance smoothly and continuously to each other, and wherein a portion of said peripheral surface on which the protuberances are disposed has a surface area that is at least 30% greater than that of a cylindrical enveloping surface, which extends along the axial extent of said portion and hugs the apices of the protuberances.

* * * * *